(12) United States Patent
Vizard et al.

(10) Patent No.: US 7,706,501 B2
(45) Date of Patent: Apr. 27, 2010

(54) METHOD AND APPARATUS FOR MEASURING LONG BONE DENSITY OF SMALL-ANIMALS

(75) Inventors: Douglas L. Vizard, Durham, CT (US); Douglas O. Wood, New Haven, CT (US); William E. McLaughlin, New Haven, CT (US); Gilbert Feke, Glastonbury, CT (US); Rao Papineni, New Haven, CT (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 12/204,132

(22) Filed: Sep. 4, 2008

(65) Prior Publication Data

US 2009/0080608 A1    Mar. 26, 2009

Related U.S. Application Data

(60) Provisional application No. 60/970,570, filed on Sep. 7, 2007.

(51) Int. Cl.
   *G01N 23/083* (2006.01)
   *G01B 15/00* (2006.01)
(52) U.S. Cl. .............................. 378/54; 378/51; 378/56; 250/583
(58) Field of Classification Search ............. 378/51–56; 250/580–585
   See application file for complete search history.

(56) References Cited

U.S. PATENT DOCUMENTS

| 4,721,112 | A |  | 1/1988 | Hirano et al. |
| 5,696,805 | A | * | 12/1997 | Gaborski et al. ............... 378/54 |
| 5,830,629 | A |  | 11/1998 | Vizard et al. |
| 6,282,258 | B1 | * | 8/2001 | Stein et al. ..................... 378/54 |
| 6,320,931 | B1 |  | 11/2001 | Arnold |
| 6,346,707 | B1 |  | 2/2002 | Vizard et al. |
| 6,366,707 | B1 |  | 4/2002 | Gardner, Jr. et al. |
| 6,444,988 | B1 |  | 9/2002 | Vizard |
| 6,546,076 | B1 | * | 4/2003 | Hull et al. .................. 378/98.3 |

(Continued)

OTHER PUBLICATIONS

Marquardt, An Algorithm for Least-Squares Estimation of Nonlinear Parameters, J. Soc. Indust. Appl. Math, vol. 11, No. 2, Jun. 1963, pp. 431-441.

(Continued)

*Primary Examiner*—Edward J Glick
*Assistant Examiner*—Anastasia Midkiff

(57) ABSTRACT

A method and apparatus are disclosed for measuring long bone density of small animals. A phosphor screen or plate is provided of a type that transduces incident ionizing radiation to emitted light. A small animal is positioned before the phosphor screen or plate and exposed to soft X-radiation having an energy level in the range of 11 to 16 Kev. Light emitted by the phosphor screen or plate is captured using a digital camera and a digital X-ray image is prepared of a long bone of the animal. The X-ray image is transformed into an X-ray density image and a region of interest is defined on the long bone in the X-ray density image. At least one row of pixels is scanned within the region of interest of the X-ray density image. A nonlinear least squares analysis of data obtained from the scanning step is conducted using a cylindrical model for the long bone within the region of interest.

8 Claims, 14 Drawing Sheets

U.S. PATENT DOCUMENTS

| | | |
|---|---|---|
| 6,990,222 B2 | 1/2006 | Arnold |
| 7,054,409 B2 | 5/2006 | Ross et al. |
| 7,469,034 B2 * | 12/2008 | Bernhardt et al. ............. 378/62 |
| 2001/0004394 A1 * | 6/2001 | Siffert et al. .................. 378/56 |
| 2002/0070365 A1 * | 6/2002 | Karellas ...................... 250/581 |
| 2003/0118152 A1 * | 6/2003 | Winsor ........................ 378/62 |
| 2006/0222223 A1 | 10/2006 | Bi et al. |

OTHER PUBLICATIONS

Haidekker et al., Computerized Methods for X-ray-Based Small Bone Densitometry, Computer Methods and Programs in Biomedicine (2004) vol. 73, pp. 35-42.

* cited by examiner

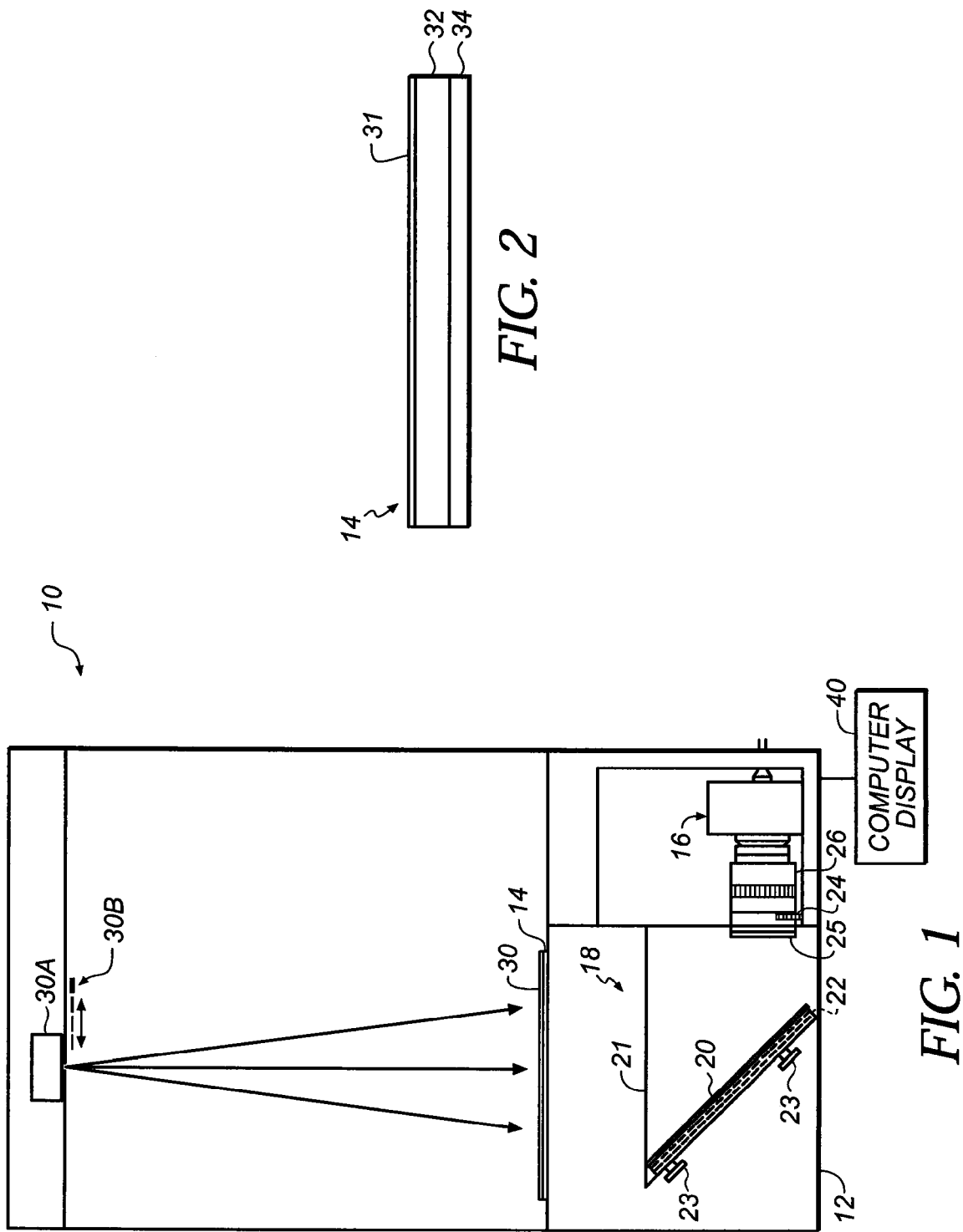

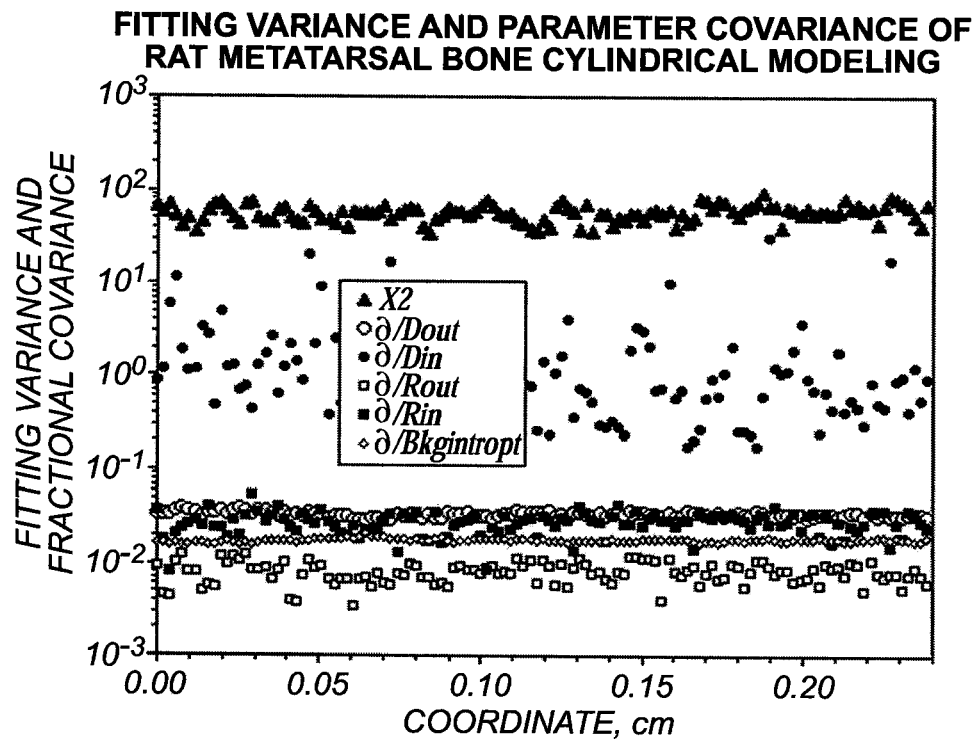
FIG. 8B1
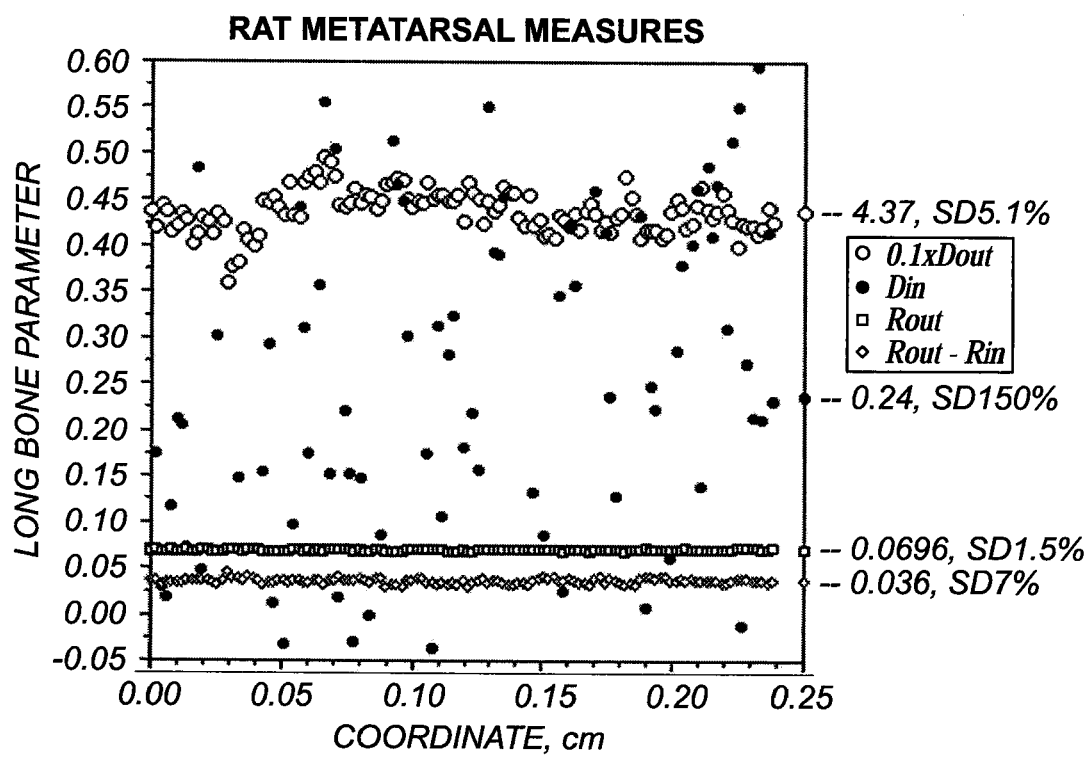
FIG. 8B2

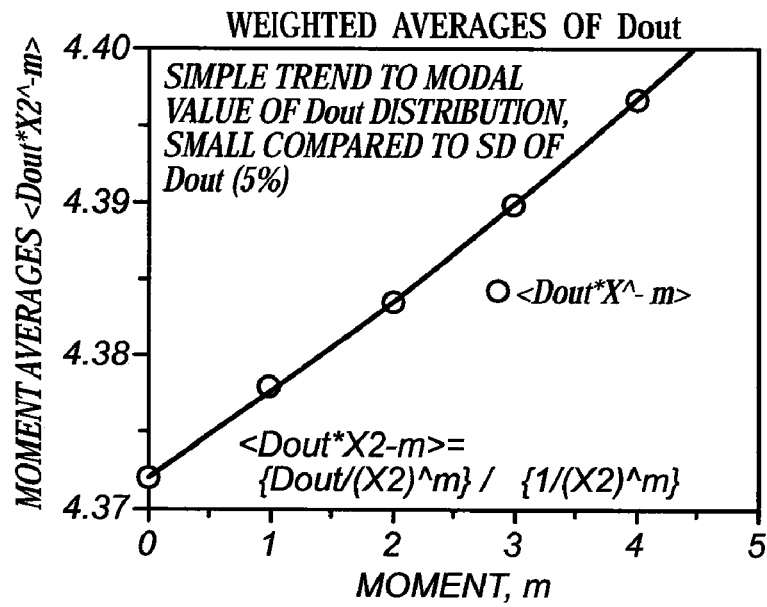
FIG. 8B3
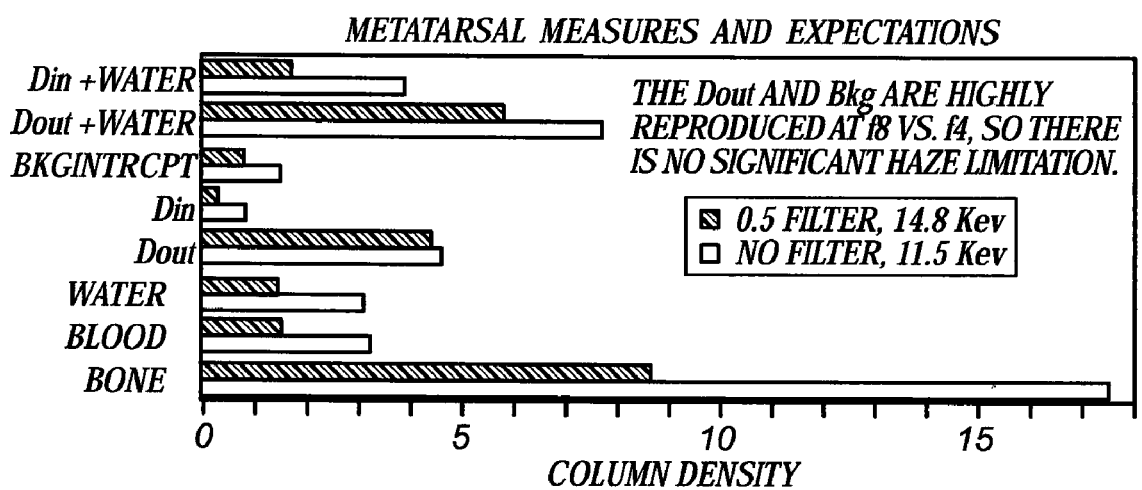
FIG. 8B4

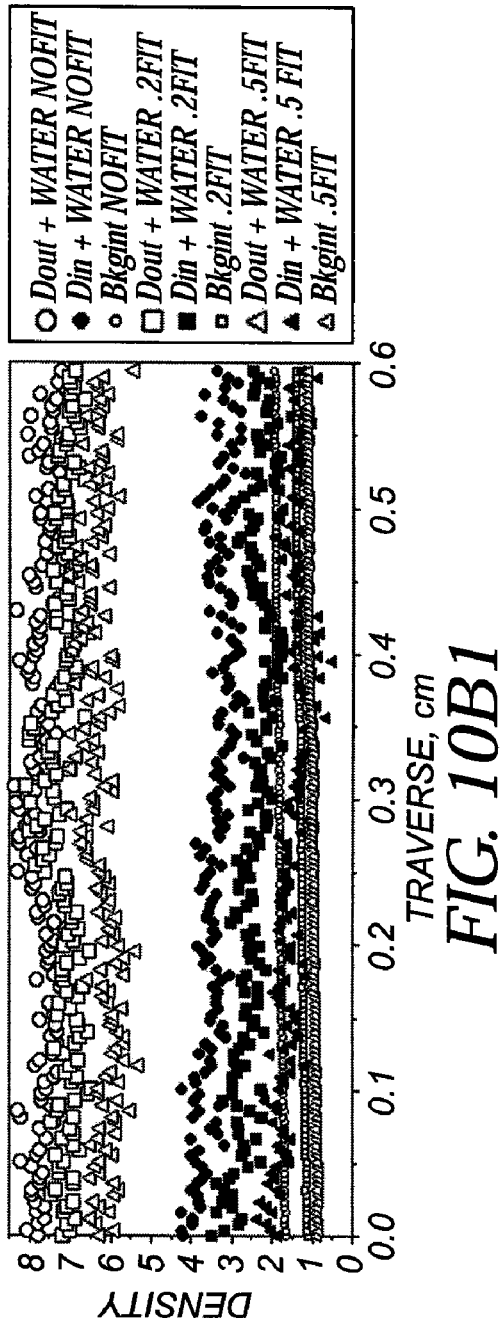
FIG. 10B1
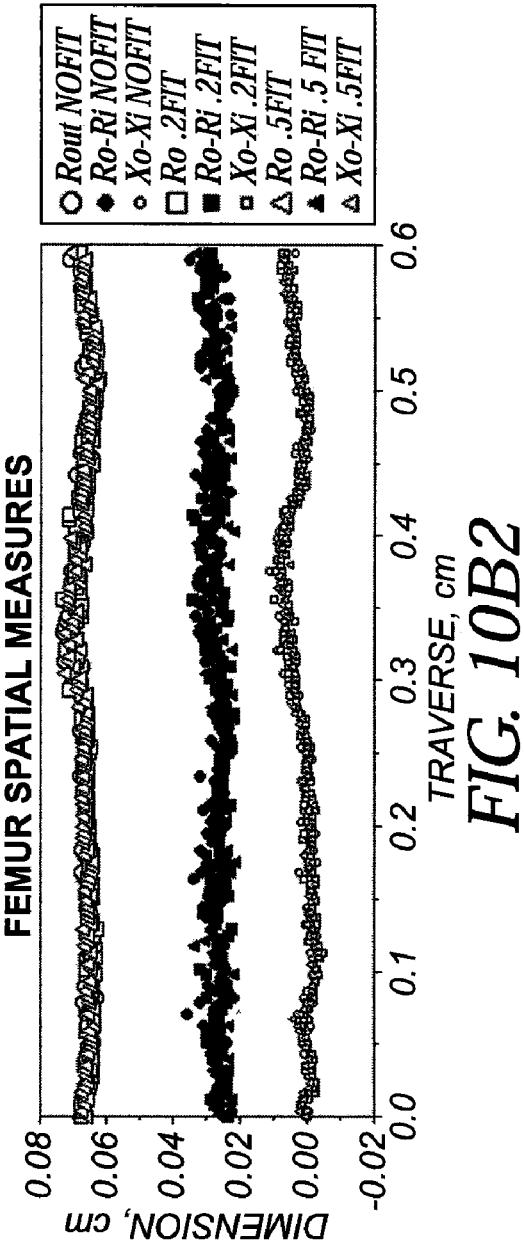
FIG. 10B2

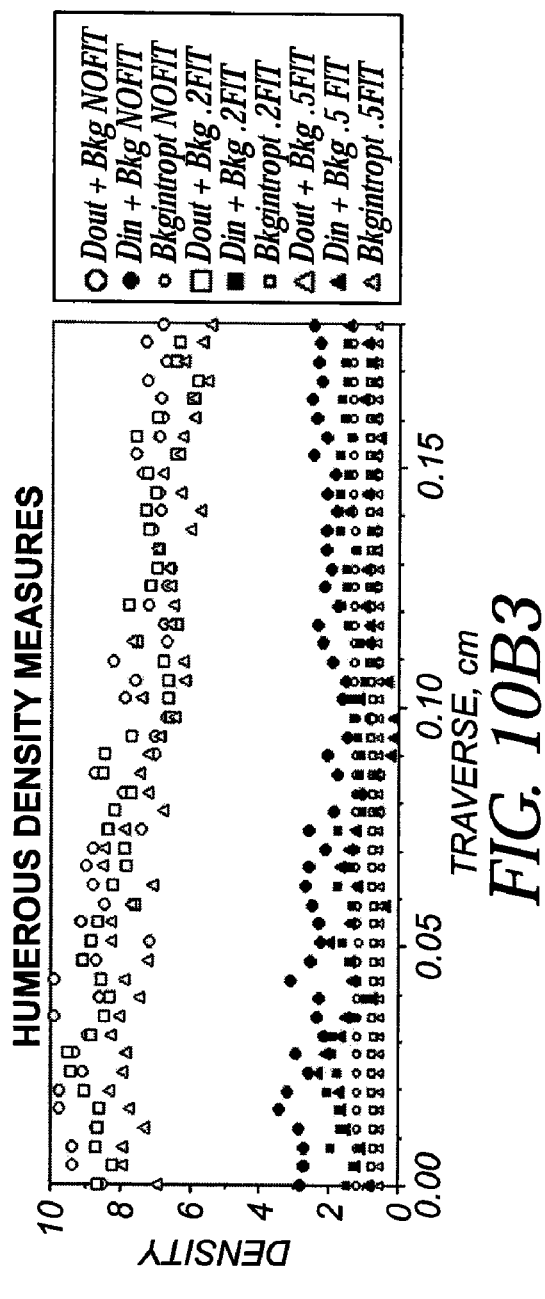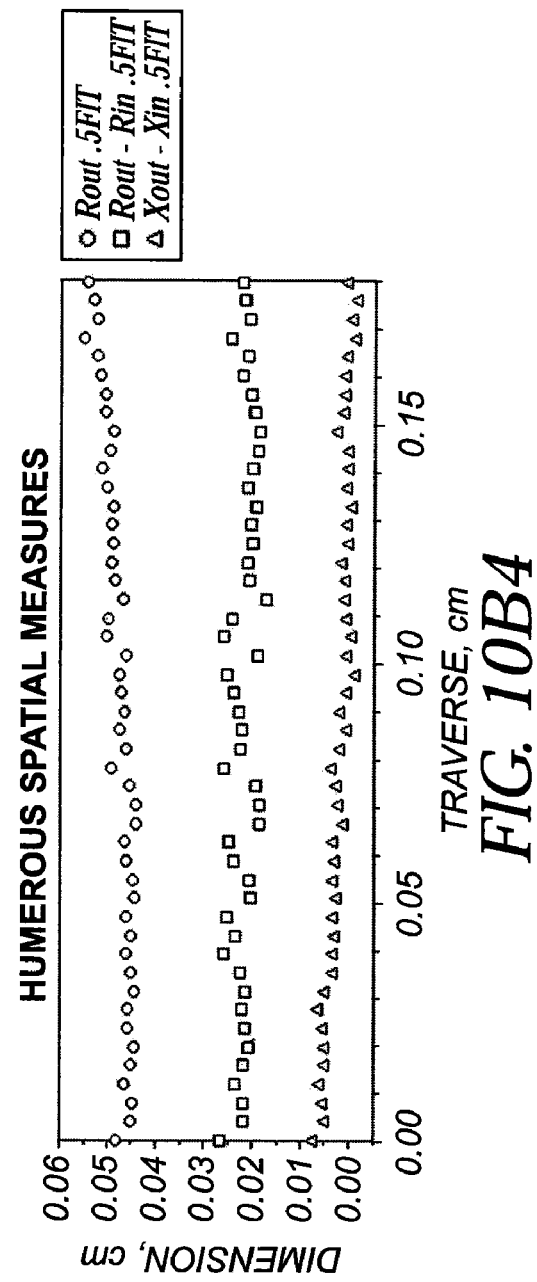

METHOD AND APPARATUS FOR MEASURING LONG BONE DENSITY OF SMALL-ANIMALS

CROSS REFERENCE TO RELATED APPLICATIONS

The priority is claimed of commonly assigned provisional U.S. patent application Ser. No. 60/970,570, filed Sep. 7, 2007 by Vizard et al, entitled "A LONG BONE DENSITY SYSTEM AND METHOD FOR SMALL-ANIMAL, LOW-ENERGY DIGITAL X-RAY IMAGING" the disclosure of which is incorporated by reference into this specification.

FIELD OF THE INVENTION

The invention relates generally to a method for measuring long bone density in a small animal using a high resolution phosphor screen, low-energy digital X-ray imaging and a software-based analytical model that yields quantitative bone and marrow density measures.

BACKGROUND OF THE INVENTION

With an increasing emphasis on small-animal disease models, radiological imaging of small animals has many of the needs that have been refined for human radiology. However, the present inventors have found that X-ray energies and image resolution that have been employed for human radiology are not easily extrapolated to small animals. For example, for quality analysis, the present inventors have found that small animal bones may require about ten times the resolution of that useful for human bones. Further, the present inventors have found that small animal bones require use of a lower range of X-ray energies due to the markedly different X-ray absorption characteristics of such small bones. Some of the best examples of film radiography may have approached the necessary spatial resolution to delineate fine bone features of small animals. The best efforts made using film radiography are known to the present inventors to present difficulties achieving adequate precision (film is insufficiently reproducible) and ergonomics (multiple films and processing time). While digital imaging is ergonomic, sufficient spatial resolution has not been clearly demonstrated. It would be desirable to have an apparatus and method capable of using high resolution phosphor screens and low energy X-rays to provide digital images sufficient for easy and efficient measurement of the long bone density of small animals.

Reference is made to commonly assigned U.S. Pat. No. 5,830,629 of Vizard et al; U.S. Pat. No. 6,346,707 of Vizard et al; and U.S. Pat. No. 6,444,988 of Vizard, each of which is incorporated by reference into this specification. Collectively, these patents disclose the essential features of a radiographic phosphor screen that may be used in the X-ray imaging system that the present inventors have found to be useful in the practice of the present invention. The technology disclosed in these patents has been used in the family of Kodak Imaging System 4000 products currently marketed by Carestream Health, Inc. These products, formerly marketed by Eastman Kodak Company, for the most part are capable of imaging objects using several imaging modalities, including X-ray, radio-isotopic, bright field and dark field (fluorescence and luminescence) modes. The IS4000 family comprises five distinct products now sold by Carestream Health, Inc. that are suitable for use in accordance with the present invention: (1) the "KODAK In-Vivo Imaging System FX"; (2) the "KODAK In-Vivo Imaging System FX Pro" which is similar to the "KODAK In-Vivo Imaging System FX" but also has a precision robotic operation (PRO); (3) the "KODAK In-Vivo Multispectral System FX" which is similar to the "KODAK In-Vivo Imaging System FX Pro" but also has more excitation filters and additional software; (4) the "KODAK Digital X-ray Specimen 4000 System;" and (5) the "KODAK Digital X-ray Specimen 4000 Pro System." The last two products are similar to the "KODAK In-Vivo Imaging System FX" and the "KODAK In-Vivo Imaging System FX Pro", respectively, except they do not have a fluorescent imaging capability.

FIG. 1 shows a diagrammatic view of an electronic imaging apparatus; and FIG. 2 shows an elevation view of a phosphor plate or screen as disclosed in previously mentioned U.S. Pat. No. 6,346,707. Such an apparatus and screen are useful in the practice of the present invention. Electronic imaging system 10 includes a housing 12, an imaging assemblage 14 (including a phosphor plate or screen), a digital camera 16 and a light transmission 18 including a mirror 20 in a mirror housing 21. Mirror 20 is supported on a foam pad 22 and adjustments 23 may be provided for adjusting the position of mirror 20. Housing 21 includes a retainer 24. Image transmission system 18 further includes a diopter 25 and a zoom lens 26. Camera 16 is connected to a computer, not shown, having a display 40 where captured images may be viewed.

An ionizing radiation source 30 may be used to produce an ionizing radiation image which is converted by imaging assemblage 14 into a light image. An auto-radiographic source 30 (such as a small animal or tissue sample treated with a suitable radioisotope) may be provided in contact with assemblage 14. Alternatively, source 30 can be located a distance from assemblage 14 and be a source of X-radiation, electron radiation, or ultraviolet radiation. In the latter case, an object to be imaged is placed on a support stage, not shown, between the source and assemblage 14 and a radiation image is projected to assemblage 14. For example, as also shown in FIG. 1, the ionizing radiation source may be an X-ray source 30A comprising an X-ray generator with a micro-focus aperture that produces a controlled emission characterized by a spot size. As shown schematically in FIG. 1, an assemblage of X-ray filters 30B (qualified Aluminum sheets of differing thickness) may be placed in the X-ray beam path to act as high pass filters, thus enabling user control of the mean energy of the X-rays that irradiate an object to be imaged. FIG. 3 shows a graphical representation of an energy spectrum of emitted X-rays in the apparatus of FIGS. 1 and 2 when used in accordance with the present invention. The spectrum is a histogram of X-ray energies (Kev, Kilo electron volts) emitted from an X-ray head with no added filtration other than a 0.005" Be window. The spectrum is from an X-ray tube operating at 30 Kvp. The peaks labeled "W" correspond to the expected from the tungsten target.

As shown in FIG. 2, imaging assemblage 14 includes a thin protective layer 31, a phosphor layer 32, a transparent support layer 34 with a boundary layer of air (not shown) between support 34 and phosphor 32. The phosphor layer 32 contains a prompt phosphor capable of absorbing an ionizing radiation image to produce a corresponding light image for capture by camera 16. Assemblage 14 is removable from the optical path shown in FIG. 1 in order to accommodate other optical modes imaging. The phosphor layer or screen may take any convenient form as disclosed in the three Vizard patents previously mentioned.

U.S. Patent Application Publication No. 2006/0222223 of Bi et al. discloses using a mammography device to obtain an image of a human finger bone and to analyze the bone's condition with computer-aided diagnosis (CAD) software. Bi does not discuss the use of the mammography device for determining the bone density in small animals such as rats and mice.

U.S. Pat. No. 7,054,409 of Ross et al. discusses how computed tomography (CT) detectors may not provide sufficient resolution to accurately resolve structures on the order of 0.5 to 1.5 mm and how the lack of resolution may be problematic in applications where greater resolution is desired, such as inner ear imaging, cardiac and vascular imaging, small animal imaging, and oncological screening. Ross discloses a method and device for imaging small bones such as those in small animals but does not discuss the use of such as device to determine the density of the bones that were imaged.

U.S. Pat. No. 6,320,931 of Arnold discloses a low cost X-ray bone densitometer capable of measuring bone density in the human body. The method described requires the use of a calibration phantom such as calcium hydroxyapatite in a solid tissue equivalent matrix to form the reference calibration phantom, which is positioned adjacent to the fingers for simultaneous calibration on each exam.

U.S. Pat. No. 6,990,222 of Arnold uses a number of computed tomography (CT) calibrations and beam hardening corrections based on idealized phantoms, which are often circular in shape and composed of water, plastics, or other synthetic materials. U.S. Pat. No. 4,721,112 of Hirano et al. discusses a method for bone evaluation carried out by determining a bone density distribution, from the modified bone pattern, by setting a bone model having an elliptic bone cross-sectional external shape, a zonate bone cortex, and a bone density decreasing portion in the inside of the bone cortex. The bone density distribution in each portion is classified, by color, based on the density values, and the X-ray image or photon absorptiometry image is converted to the image of the bone density distribution.

In an article entitled "Computerized methods for X-ray-based small bone densitometry" published in Computer Methods and Programs in Biomedicine (2004), 73, 35-42, Haidekker et al. describe a method for measuring bone density of small animals in which photographic film is used to capture an X-ray image. The film then is scanned to produce a digitized image that is analyzed to produce density measurements. The authors describe a considerable effort devoted to calibrating films using images considered acceptable. There is no recognition of the significance of low X-ray energy levels and high resolution phosphor plates to provide useful X-ray images in the manner disclosed by the present inventors.

SUMMARY OF THE INVENTION

The present invention offers several advantages, not all of which are incorporated in a single embodiment. A method is disclosed for measuring long bone density in small animals, using existing X-ray equipment having a radiographic phosphor screen and operating at low energy levels, plus a software-based analytical model. The X-ray energy spectrum and the image resolution of the existing equipment operate within ranges more applicable to small animal bones. By using cylindrical modeling for long bones, the invention enables bone density measurements using the fewest assumptions. This invention has been developed for the quantitative measures offered by digital radiography.

A method and apparatus are disclosed for measuring long bone density of small animals. A phosphor screen or plate is provided of a type that transduces incident ionizing radiation to emitted light. A small animal is positioned before the phosphor screen or plate and exposed to soft X-radiation having an energy level in the range of 11 to 16 Kev. Light emitted by the phosphor screen or plate is captured using a digital camera and a digital X-ray image is prepared of a long bone of the animal. The X-ray image is transformed into an X-ray density image and a region of interest is defined on the long bone in the X-ray density image. At least one row of pixels is scanned within the region of interest of the X-ray density image. A nonlinear least squares analysis of data obtained from the scanning step is conducted using a cylindrical model for the long bone within the region of interest.

BRIEF DESCRIPTION OF THE DRAWINGS

FIG. 1 shows a diagrammatic elevation view of an electronic imaging apparatus useful in accordance with the invention.

FIG. 2 shows an elevation view of a phosphor plate or screen assemblage useful in the apparatus of FIG. 1.

FIG. 4 illustrates the measured resolution using a radiographic phosphor screen in an IS4000 system.

FIGS. 8B(1) to 8B(4) show results of analysis of the ROI of FIG. 8A.

FIGS. 10B(1) to 10B(4) show results of analysis of ROIs of FIG. 10A.

DETAILED DESCRIPTION OF THE INVENTION

The apparatus of FIGS. 1 and 2 and each of the previously mentioned IS4000 family of image systems, when equipped with a Kodak Radiographic Phosphor Screen, are suitable for use in accordance with the invention. The enabling phosphor screen assemblage of FIG. 2 has a protective layer 31 that also blocks stray light, a thin phosphor layer 32 of about 25 μm (sufficiently thin to accommodate the essential resolution), and optical coatings on support layer 34 to further manage stay light. The combination of quality manufacturing of a thin phosphor and stray light management constitutes the essential function of the preferred screen.

These systems can provide an unfiltered X-ray beam (0.005" Beryllium window only), whose nominal spot size is <50 μm. More refined measures estimate a spot size of about 33 μm operating at 35 Kvp and 150 μa. The X-ray beam can be operated continuously at 12-35 Kvp and 150 μa. The source to sensor distance is 500 mm. The measured energy spectrum is shown graphically in FIG. 3.

Image Resolution

Figure 4A:
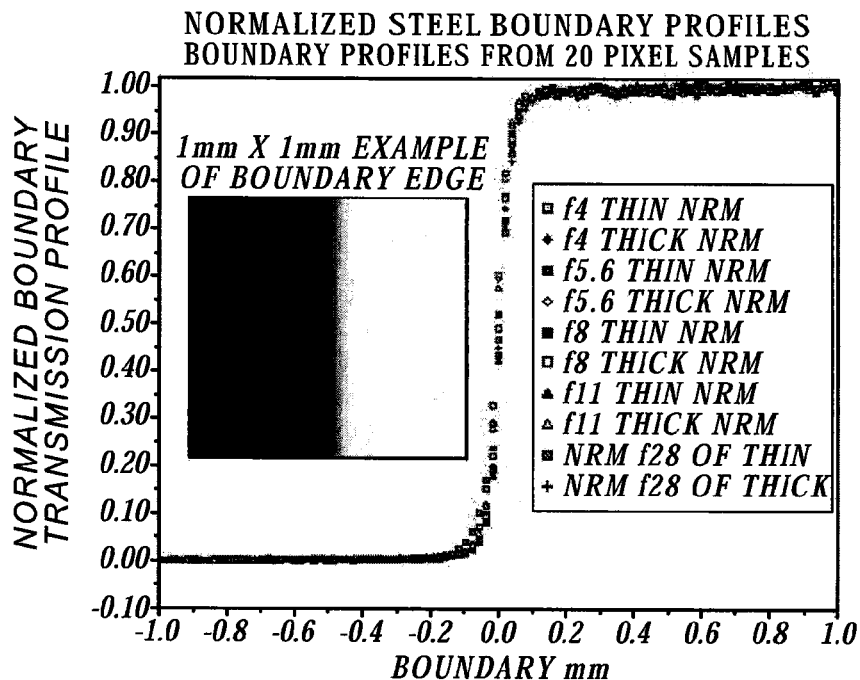
FIG. 4A shows scanned profiles across a steel boundary image (inset in graph). Differing profiles are for differing steel thickness and camera apertures.
Figure 4B:
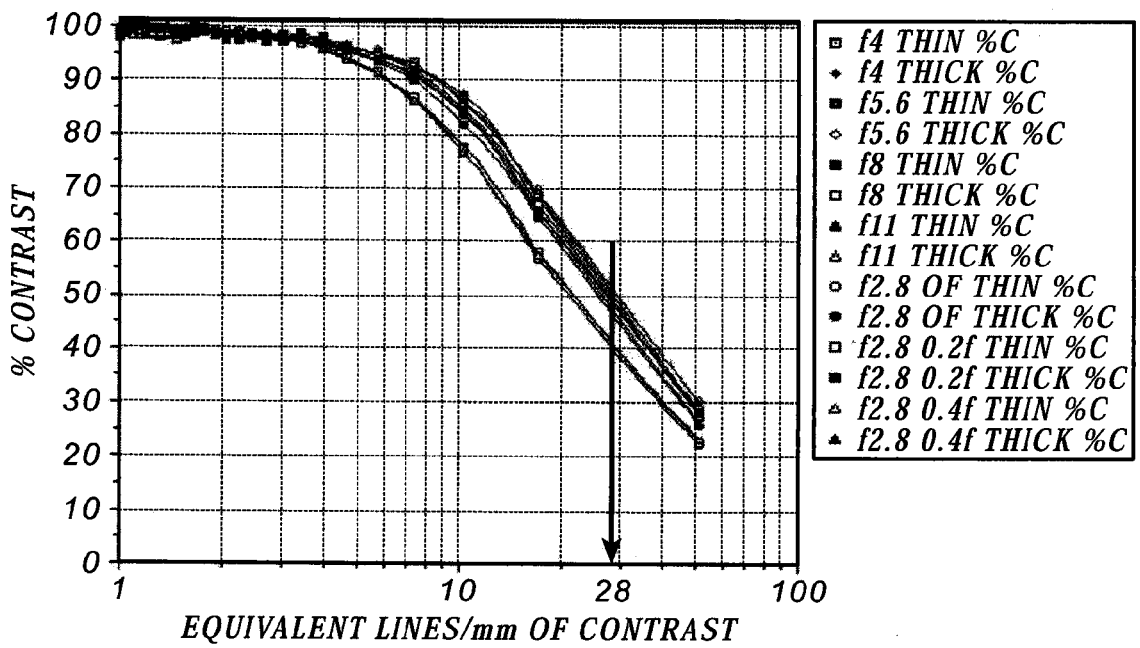
FIG. 4B shows profile analyses reduced to commonly used modulation transfer function (MTF) analysis, showing that spatial resolution essentially is invariant with tested conditions, with the exception of larger camera apertures (f/2.8). The 50% MTF criterion places the spatial resolution at 28 Line Pairs/mm.
Figure 4C:
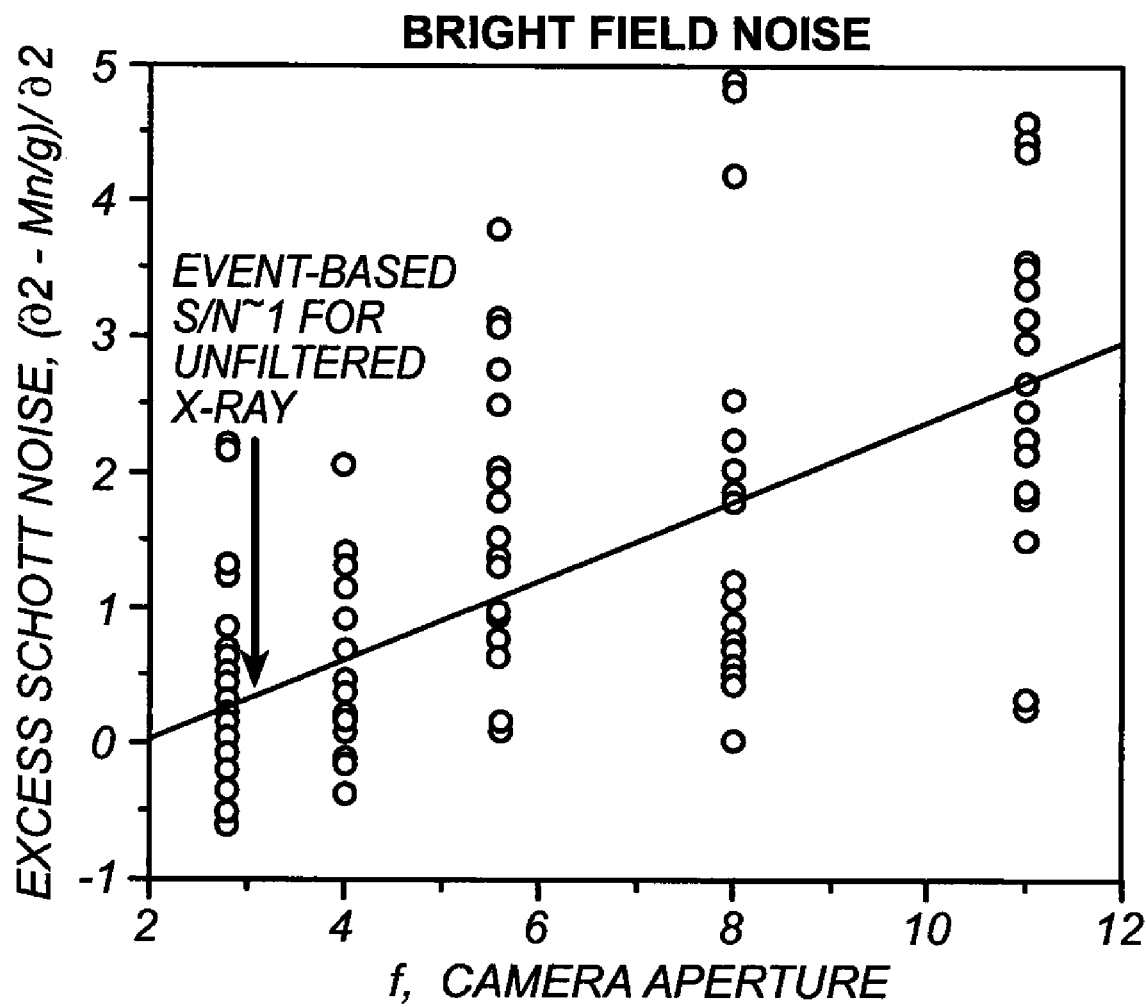
FIG. 4C shows the signal resolution analysis indicating that the system detection is limited by X-ray event statistics rather than any other overwhelming structured noise artifact of the screen or system.

A phosphor screen of the type shown in FIG. 2 includes layers such as a thin phosphor that produces light, creating a fluoroscopic image that conserves the spatial resolution limited by the micro-focus spot size. The measured spatial resolution is shown in the FIGS. 4A, 4B and 4C for the preferred KODAK Radiographic Phosphor Screen as used in IS4000 products. FIG. 4A shows how image analysis of a steel edge provides a system resolution measure that translates to a 50% MTF of 10-30 line-pairs/mm. At a 40 mm FOV the system resolution is more limited by the spot size of the micro-focus X-ray beam (<50 μm) than by the pixel size (<20 μm) of the digital camera. Resolution depends upon camera aperture, clearly shown in the analysis of FIG. 4B. Further, a signal resolution approaching that which is limited by X-ray event statistics and which is reasonably free of fixed or structured noise inherent in this (or any) imaging system is shown in shown in FIG. 4C. It is further established that the IS4000 system with a KODAK Radiographic Phosphor Screen does indeed respond linearly to X-ray dose. The system is a precise analytical imaging system wherein the X-ray density of any subject material (any object interposed between the X-ray output and the screen) can be ascertained by transforming the signal of each pixel of an image, using known software techniques with Ln (Io/I), where "Io" is the signal of accumulated X-rays that are not absorbed, and "I" is the signal of accumulated X-rays that are partially absorbed by the subject material. The analytical X-ray density ($\mu$=Ln(Io/I) can be established by the IS4000 system. This is done as described by an automatic feature by the system software, and is a precision measure of X-ray density that is chiefly limited by the number of X-rays that are absorbed/transmitted by the subject material. To promote a reasonable, practical precision of an X-ray density measure, a material must absorb about 10% of the X-rays ($\mu$~0.1); so that, typical digital 16-bit scale can accumulate sufficient signal to support the precision of measure. In order to achieve the aforementioned measurement precision, the present inventors have found that the IS4000 system preferably is operated at a range or mean of X-ray energy that "tunes" the density of the smallest bones and flesh of interest in a mouse to a density of about 0.1. More particularly, the present inventors have found that the range of X-ray energy is approximately 10-15 Kev, generally called "low energy" or "soft" X-rays. A range of 11 to 16 Kev also has been found useful.

It is recognized that the resolution of a feature within a subject diminishes with subject thickness and displacement from image or X-ray beam center due to the effects of parallax or penumbra. The present inventors have found that such resolution problems can be mitigated by using an appropriate source-to-sensor distance (approximately 500 mm) of the IS4000 system. Such a sensor distance sufficiently diminishes the detrimental penumbra of off-axis mouse features to a dimension comparable to the inherent limitation of the micro-focal spot size.

To summarize FIG. 4 and associated discussion, the IS4000 X-ray digital imaging hardware, when used with a KODAK Radiographic Phosphor Screen or equivalent screen, accommodates a level of spatial and signal resolution that enables a level of measurement precision. This level of precision is sufficient to accommodate mathematical modeling of a long bone as described below in accordance with the invention. Somewhat less spatial or signal resolution may be sufficient to apply the mathematical models; however, mock trials with half the stated resolution suggest that convergence of mathematical fits seems to fail.

Energy Calibration

Figure 3:
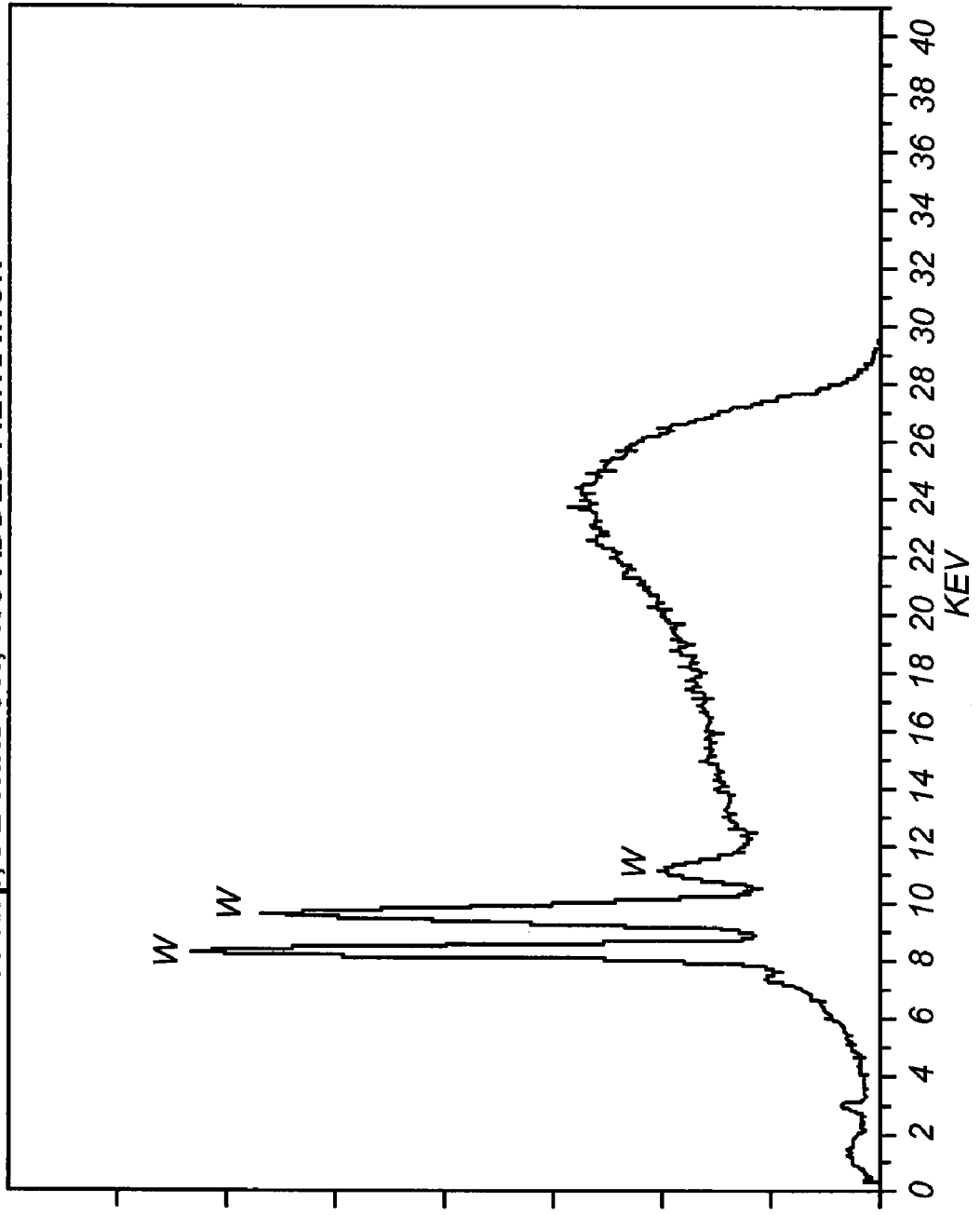
FIG. 3 is a graphical representation of the measured energy spectrum of emitted X-rays used in the apparatus of FIGS. 1 and 2 in accordance with the present invention.
Figure 5A:
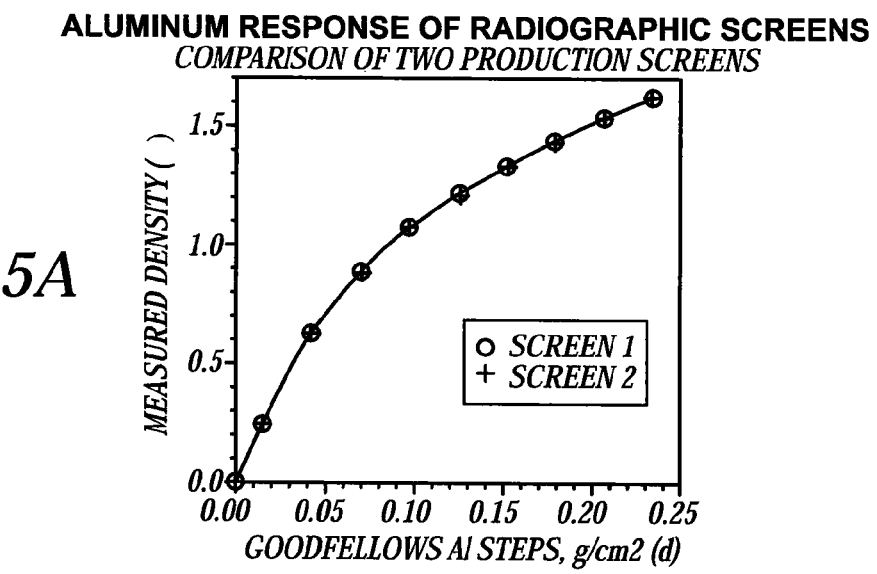
FIGS. 5A, 5B and 5C show graphical representations of average energy measures using differing thicknesses of a standard aluminum.
Figure 5B:
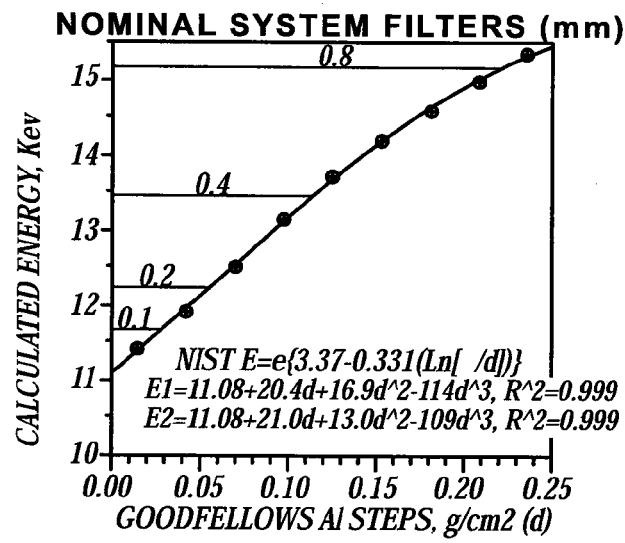
Figure 5C:
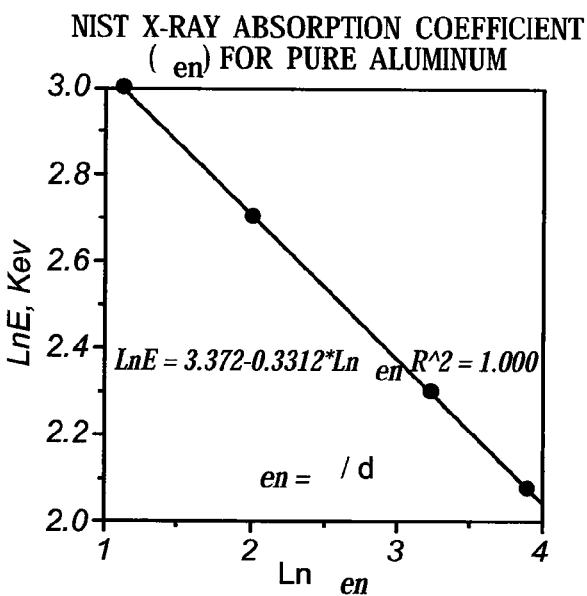

The average X-ray energy measures using differing thicknesses of standard aluminum are shown in FIGS. 5A, 5B and 5C, which show typical results for an energy calibration for the IS4000 X-ray imaging system used to support the current invention. For any radiographic phosphor screen or sensor used in the IS4000 system, the relative attenuation of standard aluminum filters is determined; the relative attenuation is transformed to attenuation to standard X-ray density ($\mu$=Ln (Io/I)); and the measured density of aluminum equated to mean the X-ray energy using NIST estimates. A selection of similar filters can be automatically managed in some versions of IS4000 system hardware; and software directs the filter placement, exposure and calculations to calibrate the system according to standard aluminum attenuation. The calibration is reduced to an equation relating average X-ray energy. The calibration shows a mean energy range of 11-16 Kev that is attained using the corresponding Al filters. The range of mean energies is consistent with the complex average of the broad energy spectra as shown in FIG. 3. The system low-energy sensitivity is limited by the air column between source and sensor, and the high-energy efficiency is limited by thickness of phosphor screen or plate 31, as in FIG. 2. The practice of calibrating low energy X-ray response is complicated by the complex energy spectrum and the handling of very thin aluminum filters. A feature of the version of the IS4000 system hardware that adds support to the present invention is the combined automated hardware and software that uses protected aluminum filters and an appropriate algorithm to perform the energy calibration. Alternatively, the person skilled in the art will understand that calibration could be done manually for systems with previously supplied manual filters, for example a known skill to radiologists. The filter used for any particular image and the calculated/calibrated mean energy are documented within the digital image file for subsequent use. Such an automated self-calibration enables the further analysis of subject material density (such as bone) using multiple X-ray energies associated with multiple image files.

The X-ray imaging system as described above is optimized to measure 0-5 cm of water or 0-1 mm of dense bone, where the signal attenuation will respond in the most precise linear dynamic range of densities of $\mu$=0-3. The present invention extends the density measurement precision to the low range of density bone features (<10 mg/cm2) that is essential for analysis of small rodent bones. Together with a spatial resolution exceeding 25 Line Pairs/mm, this energy range is particularly accommodating to the resolution of small animal constituents (as elaborated in the discussion of FIG. 4, above).

Modeling

In the present invention, an idealized three dimensional model of a mammalian long bone embedded in an inhomogeneous medium is used to predict the measured two dimensional digital image of X-Ray density variations. Use of the term "long bone" is a matter of convenience in this text for simply identifying the long, cylinder-like bones having a lumen of "marrow"—such usage is not anatomically correct. Although a cylindrically symmetric model is used in the present embodiment, a geometry that approximates the physical structure of the bone and the medium surrounding it could be used without altering the fundamental idea of the invention. Such model-assisted measures have been previously used in human radiography, as described in the previously mentioned patent of Hirano et al. One advantage of applying a cylindrical model to the radiographic image of a long bone is that few assumptions need be made regarding the context of medium, so the actual bone density measure may be more precisely related to a materials density in a live animal. Relating the bone density to known materials attenuation coefficients adds to measurement validation and lends credence to the quantitative interpretation that is sought for small-animal disease models.

To apply a cylindrical model, the inventors have assumed that the long bone resides in a tissue medium of reasonably uniform X-ray density and thickness. Particularly, the inventors have assumed that the X-ray densities of the various aggregates of bone and tissue are additive, where the X-ray density is defined by $\mu = -\text{Ln}\{I/Io\}$ (where I/Io is the fraction of absorbed X-rays): and the measured density $\mu = \Sigma_i[\mu_i' \rho_i t_i]$ is the sum of the aggregate components having an attenuation coefficient of $\mu_i'$, a mass density of $\rho_i$ and a thickness $t_i$.

The model used in accordance with the present invention uses the measured X-ray density $\mu$ to provide a measure of column density $d = \mu/t = \mu' \rho$ that is characteristic for a specified material at particular enrichment (mass density). The column density that is modeled is that of the medium plus any increment (decrement) of column density that contributes to the medium. Thus, the bone or marrow column densities that are measured using the model are added to the medium column density to predict the actual bone or marrow density. Since the medium is "soft tissue", the medium column density may be accurately estimated as water. At increased X-ray energies, the additive density of the medium decreases, so any error in the estimated medium density becomes less significant.

Figure 6:
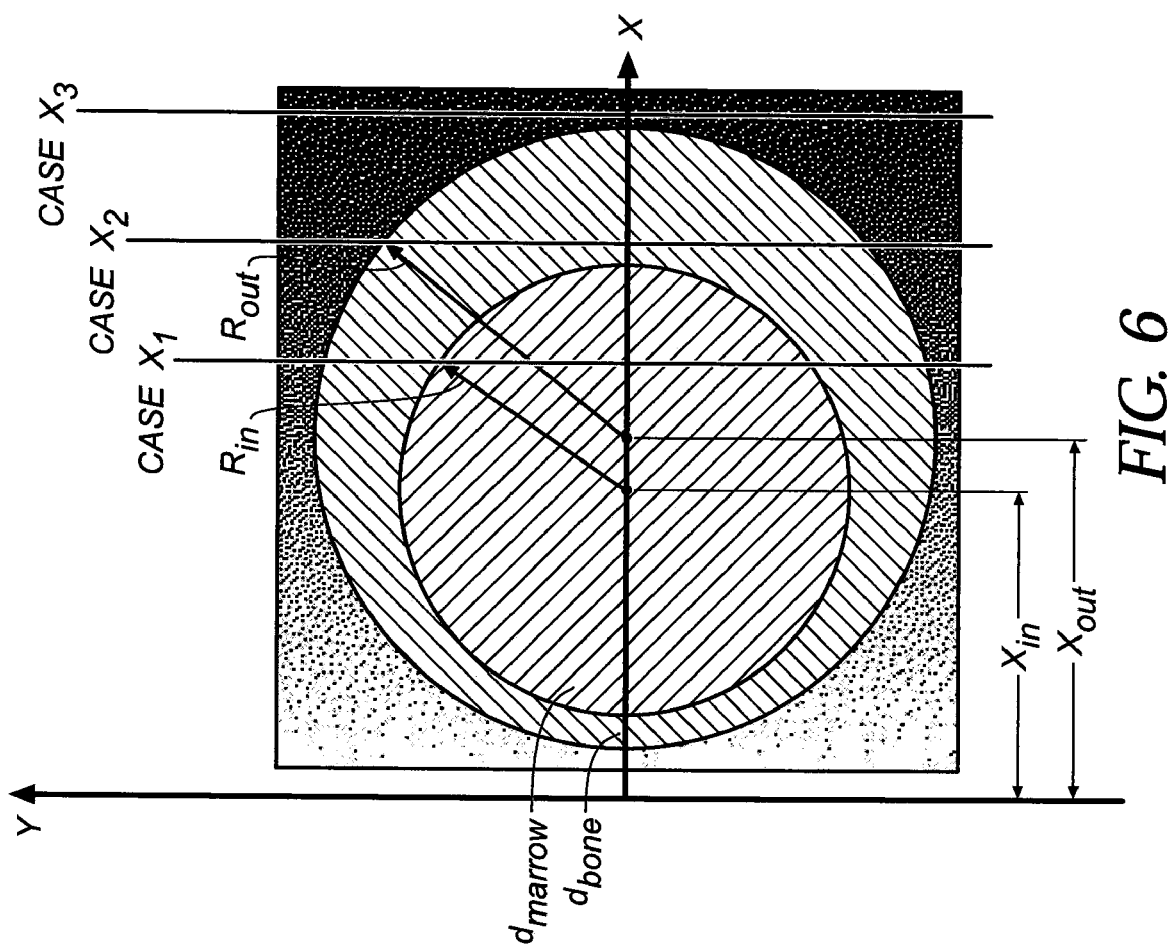
FIG. 6 is a schematic illustration of a bone cross-section containing marrow.

An advantage of the present invention that distinguishes it from the teachings of Hirano et al is that a multi-parameter mathematical fit (non-linear least squares analysis) can be performed for a sampled long-bone segment, wherein a sufficient image resolution and measurement precision enable a simultaneous mathematical solution for all the density and spatial parameters of interest. The model used in the invention now is described. As illustrated in FIG. 6, a linear coordinate traverses the bone cross section in the "x" direction (ideally perpendicular to the long bone dimension). A small animal bone has a column density $d_{bone}$ in the surrounding bone that contains a marrow of column density $d_{marrow}$ with the bone residing in a medium of density "bx+a" which may vary as a gradient of densities, approximated by a straight-line interpolation through the bone cross section. As illustrated, a linear coordinate traverses the bone cross section in the "x" direction (ideally perpendicular to the long bone axis of symmetry). The inner and outer radii of the bone cylinder are $R_{in}$ on center $X_{in}$ and $R_{out}$ on center $X_{out}$. The centricity of the cylinder may vary where marrow center $X_{in}$ need not be the same as external bone center $X_{out}$. If $X_{out}-X_{in}$ is significantly non-zero, the bone is "acentric".

The model reduces to three cases where an X-ray traverses the bone, marrow and medium (CASE 1, at traverse $X_1$), the bone and medium (CASE 2, at traverse $X_2$) or the medium only (CASE 3, at traverse $X_3$).

CASE 1: if (abs(x−xin)<Rin), then $$D = 2d_{bone}(\sqrt{R_{out}^2 - (x_{out}-x)^2} - \sqrt{R_{in}^2 - (x_{in}-x)^2}) + 2d_{marrow}\sqrt{R_{in}^2 - (x_{in}-x)^2} + bx + a$$

CASE 2: else if (abs(x−xout)<Rout), then $$D = 2d_{bone}\sqrt{R_{out}^2 - (x_{out}-x)^2} + bx + a$$

CASE 3: else $$D = bx + a$$

Figure 7B:
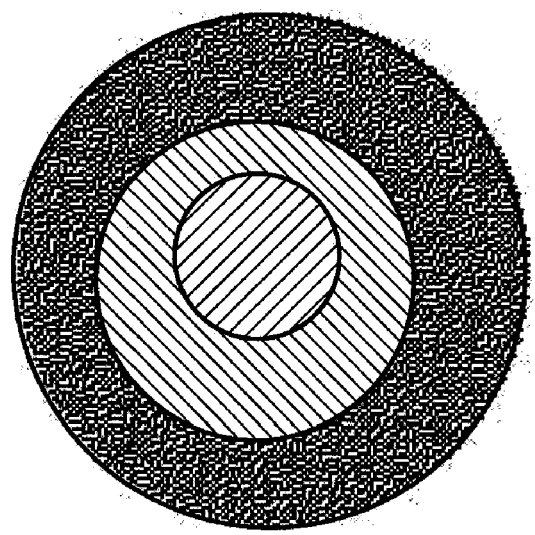
FIG. 7B shows a similar bone enveloped within tissue of close proximity.
Figure 7A:
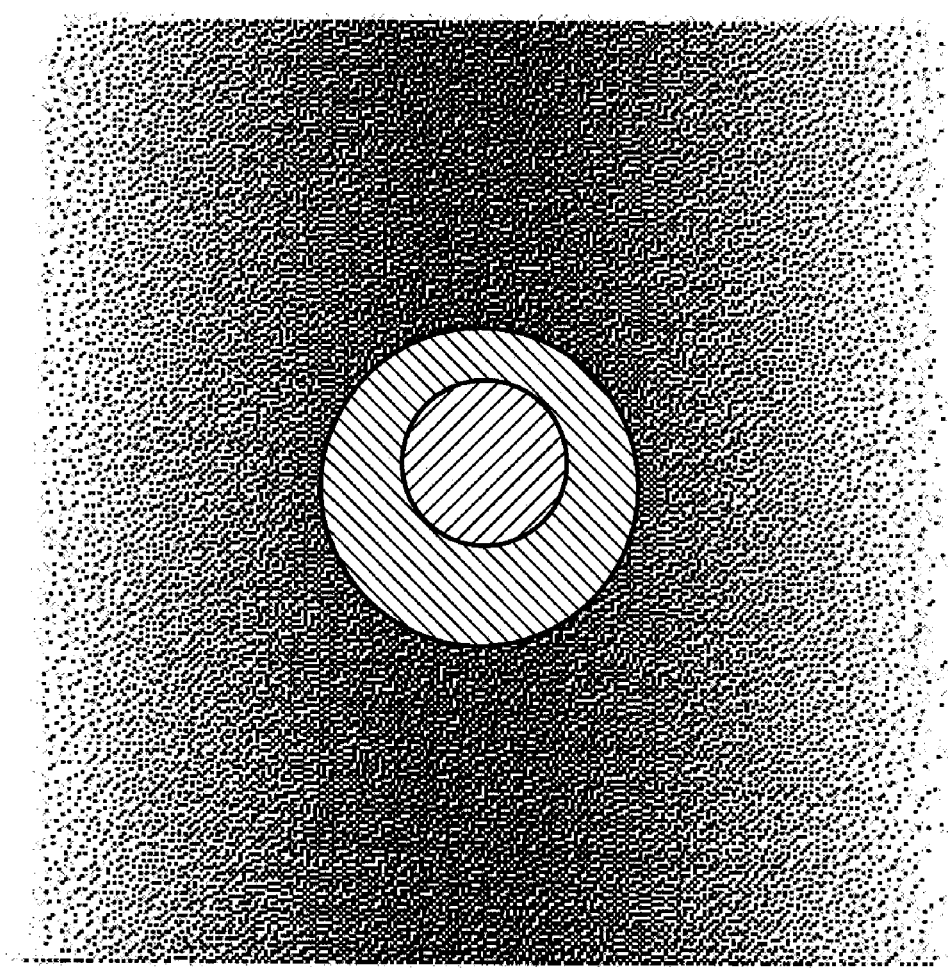
FIG. 7A shows a cross section of a long bone in a soft tissue medium with distant boundaries of unknown dimension.

Where
D=measured X-ray density along the path from the X-Ray source to a given position in the image (i.e. along the "line of sight")
$d_{bone}$=excess column density of the bone above the background column density
$d_{marrow}$=excess column density of the marrow above the background column density
$R_{out}$=outer radius of the bone
$R_{in}$=inner radius of the bone
$x_{out}$=x coordinate of the center of the outer radius of the bone
$x_{in}$=x coordinate of the center of the outer radius of the bone
b=slope of linear background density
a=intercept of linear background density FIG. 7A shows a cross section of a long bone in a soft tissue medium with distant boundaries of unknown dimension, while FIG. 7B shows a similar bone enveloped within tissue of close proximity. The cylindrical model of the present invention applies to FIG. 7A, which satisfies the basic model presumption that bone and marrow densities are incremental above a background of uniform density which may gradually vary in a linear manner. Applying the model to FIG. 7B will not yield a simple linear gradient of background density peripheral to the long bone and will incorrectly estimate the background density. Those skilled in the art will appreciate that the inventive model may be readily adapted, without departing from the scope of the invention, to cover situations such as FIG. 7B. In which case, the assumed linearly varying background (determined by parameters 'b' and 'a' ) would need to be replaced with different terms, perhaps having more variables. For FIG. 7B, for example, those skilled in the art will appreciate that the new background term would be very similar to the model for the bone (i.e. new parameters for the geometry and density of the background tissue). The model can be further adapted to relax the constraint that the centers of the cylinders of the model are co-linear with the X axis. New parameters, $Y_{in}$ and $Y_{out}$ could be added to define centers that are not on the same axis and the geometry adjusted to allow for this. Further, the inventive model may be further modified to accommodate an elliptical bone cross section as discussed in Hirano et al. A feature of the present invention is that the combined system hardware and software presents the appropriate image resolution and measurement precision essential to the convergence multi-parametric fitting estimates of bone density in small rodents.

To implement the inventive model, a digital X-ray image is transformed using known techniques in software to an X-ray density image. The digital X-ray image is captured using an imaging system such as the IS4000 system, where the image signal is quantitatively transformed to a density image by $\mu = -\text{Ln}\{I/Io\}$. The requirements for the transformation are that the subject image contains a reasonable portion of bright field background (no X-ray absorption), and that signal (I) from the sensor at each pixel is linearly related to the X-ray accumulation. The IS4000FX and other well-configured digital X-ray systems (direct or fluoroscopic) readily meet these criteria.

Figure 8A:
FIG. 8A shows a rectangular region of interest (ROI) applied to a segment of a rat metatarsal, using known analytical imaging techniques in software.

To demonstrate the inventive method, FIGS. 8A and 8B(1) to 8B(4) show how a rectangular region of interest (ROI) is applied to a segment of a rat metatarsal shown in an X-ray density image, using known analytical imaging techniques in software, as are familiar to those skilled in the art. The software permits the placement and control of the rectangle. As described below with regard to the flow chart of FIG. 9, the inventive software is able to detect symmetry of a long bone, so that it appropriately scans the cross-section of the bone, even for short bone segments. The inventive software requires that an adequate tissue domain external to the bone be sampled to evaluate background signal. Two such metatarsal ROIs are represented in FIG. 8A, and the results of their subsequent analyses are presented in FIGS. 8B(1) to 8B(4). The analyses include non-linear least-squares fitting of density profiles across the bone for each row of pixels, where the fitted results include progressive measures taken along the bone (Coordinate, cm) for bone and marrow column density ($d_{out}=d_{bone}$, $d_{in}=d_{marrow}$), outer bone radius ($R_{out}$), and bone wall thickness ($R_{out}-R_{in}$). This fitting of density profiles may be conducted using techniques known to those skilled in the art. For example, see the following discussion regarding FIG. 9. Although the model used in the inventive software can be calculated with as little as one row of pixels, the results can be improved and improved estimates can be made if several rows (cross-sections) through a uniform bone segment are averaged. In an actual example, the unusual uniformity of a metatarsal permitted 120 rows to be fitted in this case, providing extensive averaging and robust statistics showing consistent mathematical convergence. Analysis 1 of FIG. 8B shows the fitting variance and co-variance (represented as fractional) of each independent parameter, attesting to the overall precision of the estimates, with the exception of a relatively large fractional variance of the marrow. The larger fractional variance of the marrow column density is in part due to its small value (close to zero, an incremental "excess" column density), but could also reflect real micro-variations within the marrow. Further study of the variations within and among the parameters attests to the independence of the designated parameters and shows that the covariance of a measure closely approximates the standard deviation of sequential measures for this uniform long bone segment (shown in analysis 2). This analysis validates the mathematical robustness of the converging multi-parametric fit. Other validation measures are included, such as the small variation of the weighted average statistics of a normal distribution (analysis 3), and the expected energy variation of the density measures (shown in analysis 4).

The cylindrical fit with modest variation (e.g., acentricity) converges and is validated with eight parameters in the inventive model for the spatial and signal resolution provided by the existing IS4000 X-ray imaging systems. Certain modifications of the model (background tissue density, elliptical bone cross-section) may be useful, but will increase the number of parameters in the multi-parameter fit. In theory, at least a few more parameters may be tolerated before model convergence is challenged, but there will be a limit at which the multi-parametric fitting routine will not satisfactorily converge, and that limit will depend upon the practical resolution (spatial and signal).

Figure 9:
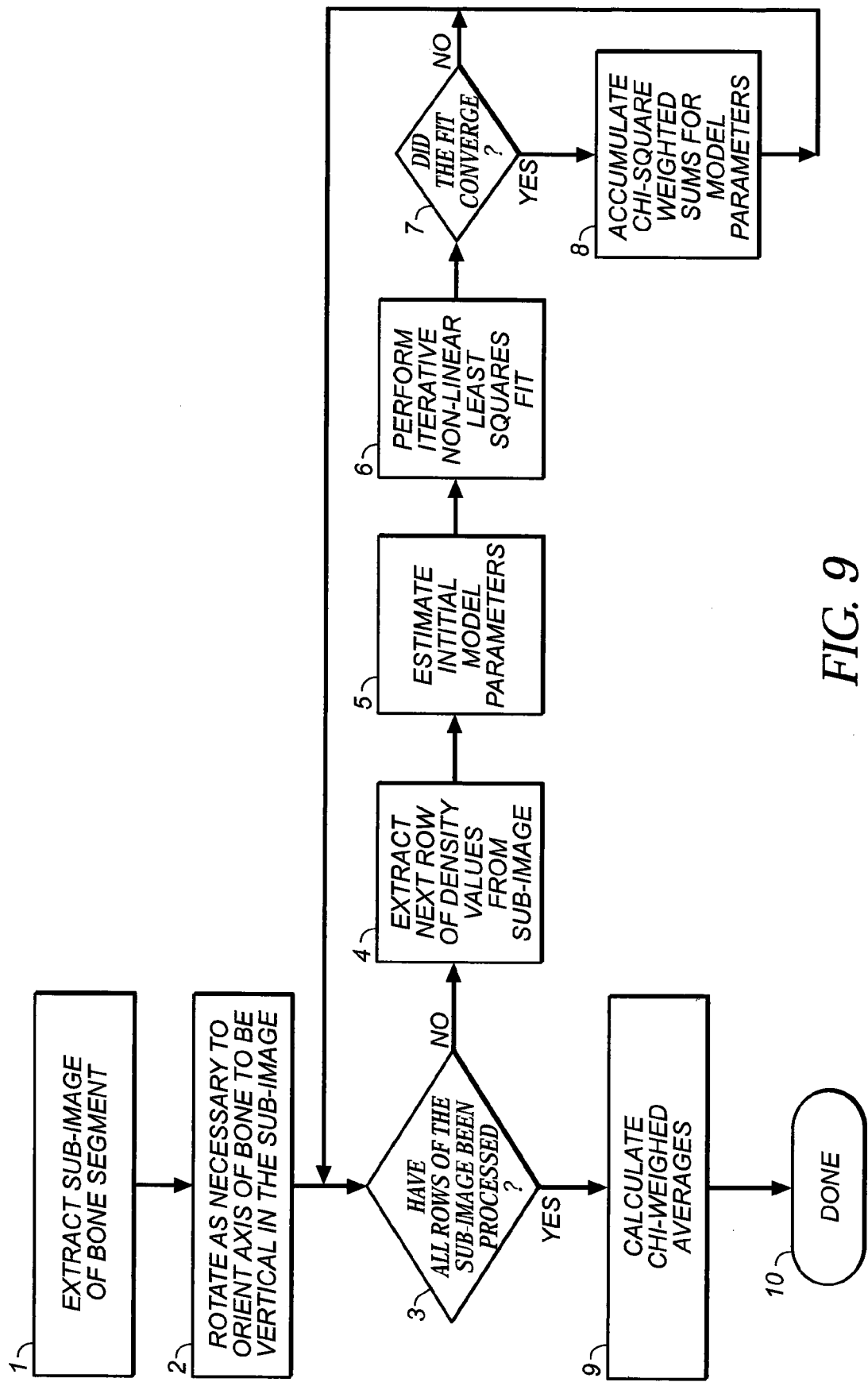
FIG. 9 shows a flow chart illustrating the basic steps of the inventive software.

FIG. 9 provides a flow chart illustrating the basic steps of the inventive software. Means for performing the described steps of the inventive method may be provided in software installed on an IS4000 system or on a separate computer, as will be understood by those skilled in the art. The required inputs to the algorithm are the X-Ray density image and a rectangular ROI (Region of Interest) that specifies to the algorithm what portion of what bone is to be used in the analysis. As known to those skilled in the art, a graphical user interface could be used to create the ROI, or it could be created automatically by a known pattern recognition process. How the ROI is created is not material to this present invention. The portion of the density image inside the ROI is referred to in the following as a sub image.

Continuing with regard to FIG. 9, in step 1 the sub image is extracted from the original image and stored temporarily in memory. Any number of sub images could be analyzed on a given image (by the creation of an ROI for each) and sub images can overlap. In step 2 the sub image is rotated (using the rotation angle of the ROI) so that the long axis of the bone is vertical in the sub image. Such a step is not strictly required since the analysis could be performed on an unrotated image; but rotating the sub image simplifies the following steps because it makes it possible to analyze the rotated image row by row. To ensure that the bone is in fact vertical (and not horizontal) in the sub image, the software then calculates the root mean square (RMS) deviation of both the first and last columns and the first and last rows of pixels. The sub image is rotated by a further 90 degrees if the columns do not have a lower RMS deviation than the rows (the RMS deviation lowest along lines that run parallel to the bone). This RMS check is not required by the algorithm but is a convenience.

In step 3 the algorithm checks to see if all rows of the sub image have been processed. For each row of the image, steps 4 through 7 (and optionally step 8) then are executed. In step 4 a linear array of density values is extracted from the sub image for the given row and stored in temporary memory. In step 5 the algorithm estimates initial values for the model parameters by examining the extracted row of density values. It is not critical to the algorithm exactly how these estimates are made. One embodiment finds the location of the highest density values on the left and on the right halves of the row. The initial value for the outer radius value is estimated by dividing the distance between the two peaks in half. The initial values for the location of the centers of the cylindrical model are calculated from the average position of the two peaks. The initial value for the inner radius is estimated to be 75% of the initial value for the outer radius. The initial values for linear background are estimated from a few pixels taken on either end of the row of data. The initial value for the marrow excess column density is set to zero. The initial value for the bone excess column density is estimated from the height of the density peaks.

In step 6 an iterative, non-linear least squares fit analysis is performed to adjust values of the model parameters so as to minimize the chi square of the residual (data minus model). It is not critical to this invention exactly what algorithm is used to perform this optimization. In one embodiment the method described by W. H. Press et al. (*Numerical Recipies*, Cambridge University Press, 1986) was used. That model is based on the Levenberg-Marquardt algorithm (Marquardt, D. W, 1963, *Journal of the Society for Industrial and Applied Mathematics*, vol. 11, pp 431-441). In step 7 the algorithm branches depending on the success of the fit for the given row. If the fit is successful (a local minimum of the chi square of the residuals is found) then step 8 is processed, otherwise, the algorithm returns to step 3 to process another row.

In step 8 the algorithm accumulates sums that will be used in step 9 to find the inverse chi square weighted average of the best fit model parameters. For example, the best fit value for the outer radius is multiplied by the inverse of the chi square value of the fit, and this product is added to a running sum of the same product for all the other successful least squares fits. The sum of the inverse of the chi square value for each fit is also accumulated in step 8. In step 9 after all the rows have been processed, the inverse chi square weighted sums of each model parameter are divided by the final sum of the inverse chi square values for all the successful fits. In this way, the method has found an estimate of the best value for each model parameter that applies a greater weight toward rows of the image that had the lowest chi square (a lower chi square value indicates the closest match between the model and the data for a given row). The process ends at step 10.

The present inventors note that, although the embodiment of the algorithm discussed with regard to FIG. 9 fits each row of data independently, the algorithm could be modified to fit the entire sub image at once, though this would be considerably more complicated and could require more processing time. The inventors also note that even if the cylindrical model used in the embodiment discussed with regard to FIG. 9 were to be replaced with a different geometrical model (e.g. an ellipsoidal cylinder) or parameters were added to the model (e.g. allow the bone column density parameter to vary with radius) or taken away from the model (e.g. require the inner and outer circles to have the same center position), the essential character of the method would remain unchanged. That is, transformed X-Ray density values measured from a two dimensional X-ray projection of a bone embedded in surrounding tissue (or no tissue) are fit with a iterative procedure that optimizes the parameters of the three dimensional cylindrical model for the bone and marrow density. The inventors note that this same method could be applied to human or large animal bones with a suitable adjustment in the mean X-Ray energy used and the required spatial resolution. The inventors further recognize that these density measures are designed to accommodate in-vivo measures, implying applicability to repeated measures on a live animal which anticipates the application of these measures to disease detection or progression and to bone development.

Figure 10A:
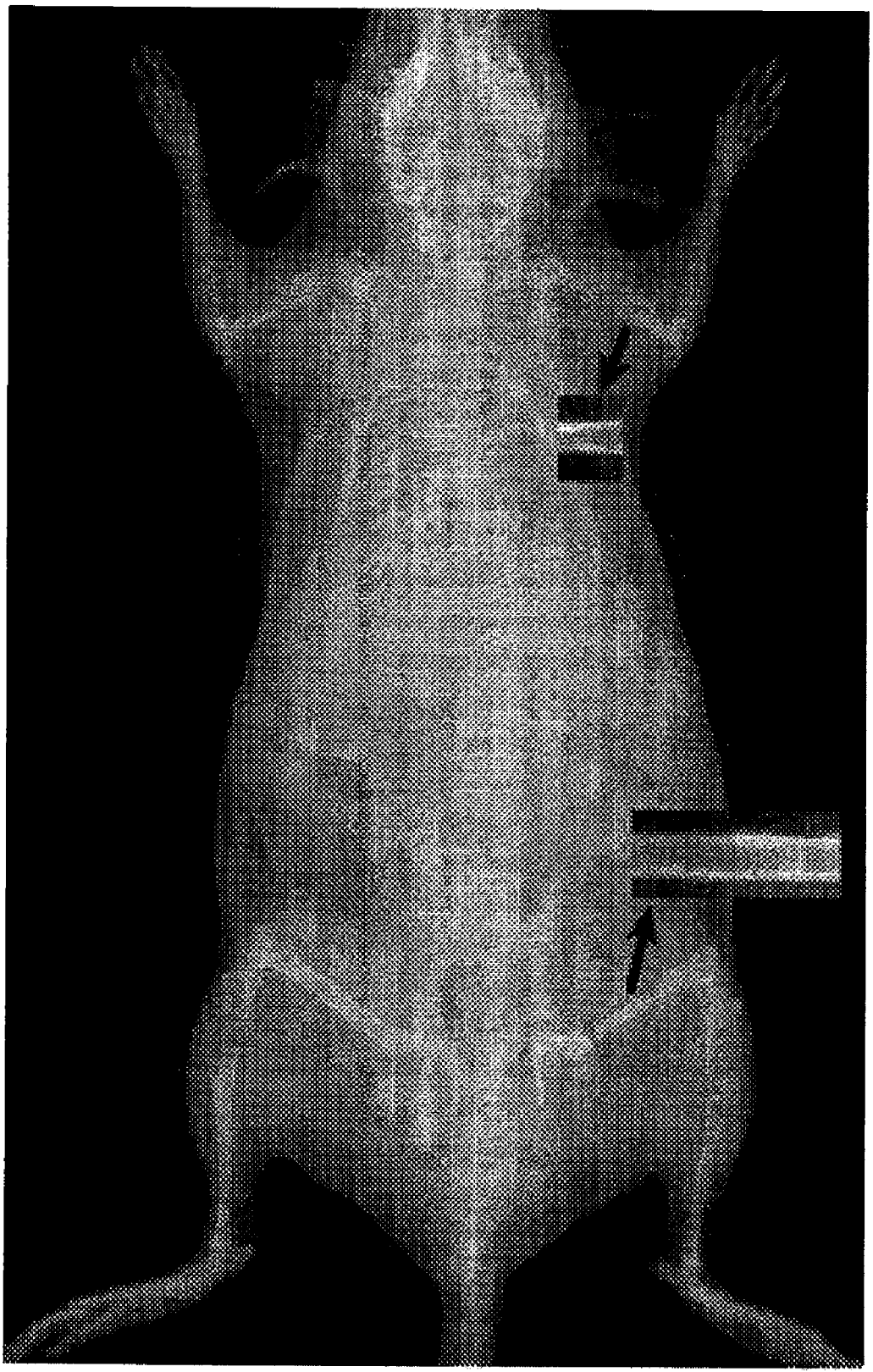
FIG. 10A shows other examples of mouse femur and humerus measures made in accordance with the present invention.

Other examples of mouse femur and humerus measures are shown in the FIGS. 10A and 10B(1) TO 10B(6), where variations along the bone can be tolerated and measured by the inventive model. FIG. 10A shows the ROI for segments of a mouse femur and humerus. For instance in FIG. 10B(1) the femur measures a region of higher column density along the bone traverse ($d_{out}$+water), but not for the marrow ($d_{in}$+water), and all of the density measures (including background) significantly decrease with increasing energy as expected. The energy is tuned with the filter thickness noted in legend. In FIG. 10B(2), the femur shows significant spatial variation along the segment for outer radius ($R_o$), inner radius ($R_i$), wall thickness ($R_o-R_i$) and particularly the acentricity ($X_o-X_i$). Note that the spatial dimensions are invariant with energy (as expected). The humerus measures of FIGS. 10B(3) and 10B(4) show the diverging bone diameter and diminishing density, but the wall thickness remains reasonably constant (as does the marrow density), and the acentricity significantly varies.

The cylindrical symmetry of selected long bones was used to measure the column density of rat metatarsal and mouse femur and humerus bones and marrow. Bone and marrow column densities conform to the units of 1/cm, and may be directly related to experimentally measured density $\mu=\mu'\rho t$, where the mass density $\rho$ and thickness $t$ vary independently, and $\mu'$ is an intensive materials coefficient that depends upon atomic constituents and X-ray energy. Generally, the unit of measure for coefficient $\mu'$ is $cm^2/g$. Known materials of unknown thickness are characterized in an X-ray density measure of $\mu/\mu'=\rho t$, in units of $g/cm^2$, or $mg/cm^2$ for thin materials. Differing measures may be tailored to situations where differing variables are known. In the present case using the cylindrical model for long bones, an "unknown" material of known thickness is measured as column density $\mu/t$ ($=\mu'\rho$) having the units $cm^{-1}$, and may be compared to that which is expected from pure materials listed in X-ray attenuation tables (NIST). The published attenuation coefficients are given as $\mu'=\mu_{en}/\rho$, so a mass density must be presumed to complete the comparison. The assumption that tissue density is ~1.0 g/cc is reasonable, but bone density may vary from 2.5-2.7 g/cc for hard bone, but may be much lower. Generally, the rodent bone density measures are at least 2-4 fold less than is expected from hardest bone estimates.

To ease the comparison to the nominally quoted "bone surface density", in units of $g/cm2$, the inventive software converts the measured column densities to surface density by mathematically projected the bone cylinder to a plane. A summary report of the averaged parameters of the designated bone segment (ROI) is presented. Note that the bone density and marrow density are properly separated in the inventive modeling, so they are separately reported. Further, other calibrations have been performed in separate studies (such as water and hydroxyapatite), so further estimates of background tissue depth and hydroxyapatite equivalence of bone are also reported.

The invention has been described in detail with particular reference to certain preferred embodiments thereof, but it will be understood that variations and modifications can be effected within the spirit and scope of the invention.

| PARTS LIST | |
|---|---|
| 10 | electronic imaging system |
| 12 | housing |
| 14 | imaging assemblage |
| 16 | digital camera |
| 18 | light transmission system |
| 20 | mirror |
| 21 | mirror housing |
| 22 | foam pad |
| 23 | adjustments |
| 24 | retainer |
| 25 | diopter |
| 26 | zoom lens |
| 30 | ionizing radiation source |
| 30A | X-ray source |
| 30B | assemblage of X-ray filters |
| 31 | phosphor layer |
| 32 | transparent support layer |
| 34 | transparent platen |
| 40 | display |
| Steps 1 to 10 | steps of inventive software algorithm |

What is claimed is:

1. A method for measuring long bone density of small animals, comprising:
    providing a phosphor screen or plate of a type that transduces incident ionizing radiation to emitted light;
    positioning a small animal before the phosphor screen or plate;
    exposing the animal to X-radiation having an energy level in the range of 10 to 16 Kev;
    capturing light emitted by the phosphor screen or plate using a digital camera and preparing a digital X-ray image of a long bone of the animal; and
    using a computer to perform the steps of:
        transforming the X-ray image into an X-ray density image;

defining a region of interest of the long bone in the X-ray density image;

scanning at least one row of pixels within the region of interest of the X-ray density image; and conducting a nonlinear least squares analysis of data obtained from the scanning step using a virtual, cylindrical model for the long bone within the region of interest and adjusting values of parameters of the model so as to minimize the chi square of a residual between the data and the model.

2. A method according to claim 1, wherein the phosphor screen has a spatial resolution of >25 line pairs/mm$^2$ at 50% MTF.

3. An apparatus for measuring long bone density of small animals, comprising:

a phosphor screen or plate of a type that transduces incident ionizing radiation to emitted light;

a source of X-radiation having an energy level in the range of 10 to 16 Kev;

a stage for supporting a small animal between the screen or plate and the source;

a digital camera for capturing light emitted by the phosphor screen or plate from a small animal positioned on the stage and producing a digital X-ray image of a long bone of the animal; and a computer for receiving the digital X-ray image, the computer comprising:

means for transforming the digital X-ray image into an X-ray density image;

means for defining a region of interest of the long bone in the X-ray density image;

means for scanning at least one row of pixels within the region of interest of the X-ray density image; and means for conducting a nonlinear least squares analysis of data obtained from the scanning step using a virtual, cylindrical model for the long bone within the region of interest and adjusting values of parameters of the model so as to minimize the chi square of a residual between the data and the model.

4. An apparatus according to claim 3, wherein the phosphor screen has a spatial resolution of >25 line pairs/mm$^2$ at 50% MTF.

5. A method for measuring long bone density of small animals, comprising steps of:

providing a phosphor screen or plate of a type that transduces incident ionizing radiation to emitted light;

positioning a small animal before the phosphor screen or plate;

exposing the animal to X-radiation having an energy level in the range of 10 to 16 Kev;

capturing light emitted by the phosphor screen or plate using a digital camera and preparing a digital X-ray image of a long bone of the animal;

transforming the X-ray image into an X-ray density image;

defining a region of interest of the long bone in the X-ray density image;

scanning at least one row of pixels within the region of interest of the X-ray density image; and conducting a nonlinear least squares analysis of data obtained from the scanning step using a virtual, cylindrical model for the long bone within the region of interest, wherein the cylindrical model is according to the following relationship:

CASE 1: if (abs(x−xin)<Rin), then $$D=2d_{bone}(\sqrt{R_{out}^2-(x_{out}-x)^2}-\sqrt{R_{in}^2-(x_{in}-x)^2})+2d_{marrow}\sqrt{R_{in}^2-(x_{in}-x)^2}+bx+a$$

CASE 2: else if (abs(x−xout)<Rout), then $$D=2d_{bone}\sqrt{R_{out}^2-(x_{out}-x)^2}+bx+a$$

CASE 3: else, $$D=bx+a,$$

Wherein

D=measured X-ray density $d_{bone}$=excess column density of the bone above background column density;

$d_{marrow}$=excess column density of the marrow above background column density;

$R_{out}$=outer radius of the bone $R_{out}R_{in}$=inner radius of the bone;

$x_{out}$=x coordinate of the center of the outer radius of the bone;

$x_{in}$=x coordinate of the center of the outer radius of the bone;

b=slope of linear background density; and a=intercept of linear background density.

6. A method according to claim 5, wherein the phosphor screen has a spatial resolution of >25 line pairs/mm$^2$ at 50% MTF.

7. An apparatus for measuring long bone density of small animals, comprising:

a phosphor screen or plate of a type that transduces incident ionizing radiation to emitted light;

a source of X-radiation having an energy level in the range of 10 to 16 Kev;

a stage for supporting a small animal between the screen or plate and the source;

a digital camera for capturing light emitted by the phosphor screen or plate from a small animal positioned on the stage and producing a digital X-ray image of a long bone of the animal;

means for transforming the digital X-ray image into an X-ray density image;

means for defining a region of interest of the long bone in the X-ray density image;

means for scanning at least one row of pixels within the region of interest of the X-ray density image; and means for conducting a nonlinear least squares analysis of data obtained from the scanning step using a virtual, cylindrical model for the long bone within the region of interest, wherein the cylindrical model is according to the following relationship:

CASE 1: if (abs(x−xin)<Rin), then $$D=2d_{bone}(\sqrt{R_{out}^2-(x_{out}-x)^2}-\sqrt{R_{in}^2-(x_{in}-x)^2})+2d_{marrow}\sqrt{R_{in}^2-(x_{in}-x)^2}+bx+a;$$

CASE 2: else if (abs(x−xout)<Rout), then $$D=2d_{bone}\sqrt{R_{out}^2-(x_{out}-x)^2}+bx+a$$

CASE 3: else, wherein:

$$D=bx+a;$$

where

D=measured X-ray density $d_{bone}$=excess column density of the bone above background column density;

$d_{marrow}$=excess column density of the marrow above background column density;

$R_{out}$=outer radius of the bone;

$R_{in}$=inner radius of the bone;

$x_{out}$=x coordinate of the center of the outer radius of the bone;

$x_{in}$ = x coordinate of the center of the outer radius of the bone;

b = slope of linear background density; and a = intercept of linear background density.

8. An apparatus according to claim 7, wherein the phosphor screen has a spatial resolution of >25 line pairs/mm$^2$ at 50% MTF.

* * * * *